United States Patent [19]
Hipp

[11] Patent Number: 5,756,971
[45] Date of Patent: May 26, 1998

[54] CERAMIC HEATER FOR A GAS MEASURING SENSOR

[75] Inventor: Heinrich Hipp, Hemmingen, Germany

[73] Assignee: Robert Bosch GmbH, Stuttgart, Germany

[21] Appl. No.: 256,915

[22] PCT Filed: Nov. 27, 1993

[86] PCT No.: PCT/DE93/01135

§ 371 Date: Aug. 3, 1994

§ 102(e) Date: Aug. 3, 1994

[87] PCT Pub. No.: WO94/14057

PCT Pub. Date: Jun. 23, 1994

[30] Foreign Application Priority Data

Dec. 4, 1992 [DE] Germany ............... 42 408 12.1

[51] Int. Cl.$^6$ ........................................ H05B 3/06
[52] U.S. Cl. ................. 219/537; 219/202; 219/541; 338/204; 338/260; 338/320; 338/314
[58] Field of Search ................. 219/202, 205, 219/206, 550, 551, 537, 549, 525; 338/204, 205, 246, 249, 254, 280, 288, 289, 293, 295, 314, 34, 307, 54, 239, 235, 255–257, 260, 320

[56] References Cited

U.S. PATENT DOCUMENTS

| | | |
|---|---|---|
| 1,125,889 | 1/1915 | Smith ............................ 338/249 |
| 2,518,941 | 8/1950 | Satchwell et al. ............... 338/254 |
| 3,071,749 | 1/1963 | Starr ............................. 338/314 |
| 3,518,756 | 7/1970 | Bennett et al. ................. 29/846 |
| 3,999,004 | 12/1976 | Chirino et al. ................ 29/624 |
| 4,109,377 | 8/1978 | Blazick et al. ................ 29/626 |
| 4,164,539 | 8/1979 | Johnston ........................ 422/96 |
| 4,300,990 | 11/1981 | Maurer ........................... 422/98 |
| 4,568,908 | 2/1986 | Laskaris et al. ............... 338/280 |
| 4,630,024 | 12/1986 | Allen ............................ 338/280 |
| 4,697,165 | 9/1987 | Ishiguro et al. ............... 338/34 |
| 4,883,947 | 11/1989 | Murase et al. ................. 219/553 |
| 5,199,791 | 4/1993 | Kasanami et al. .............. 338/314 |
| 5,332,991 | 7/1994 | Kojima et al. ................. 338/314 |

FOREIGN PATENT DOCUMENTS

| | | | |
|---|---|---|---|
| 569248 | 4/1961 | Belgium ........................ 338/293 |
| 4006085 | 8/1991 | Germany . | |
| 3248053 | 11/1991 | Japan .......................... 338/34 |
| 91/09301 | 6/1991 | WIPO . | |

*Primary Examiner*—Teresa J. Walberg
*Assistant Examiner*—Karl Easthom
*Attorney, Agent, or Firm*—Spencer & Frank

[57] ABSTRACT

Proposed is a heater arrangement for a measuring sensor for determining components in gases, particularly in exhaust gases of internal combustion engines. The heater arrangement comprises at least two heating elements (10, 11) which are disposed at least partly one above the other and electrically insulated from one another by means of at least one insulating layer. A contacting member (14) laid through the insulating layer from one heating element (10) to the other heating element (11) is provided in such a manner that the heating elements (10, 11) are switched in series one behind the other.

10 Claims, 4 Drawing Sheets

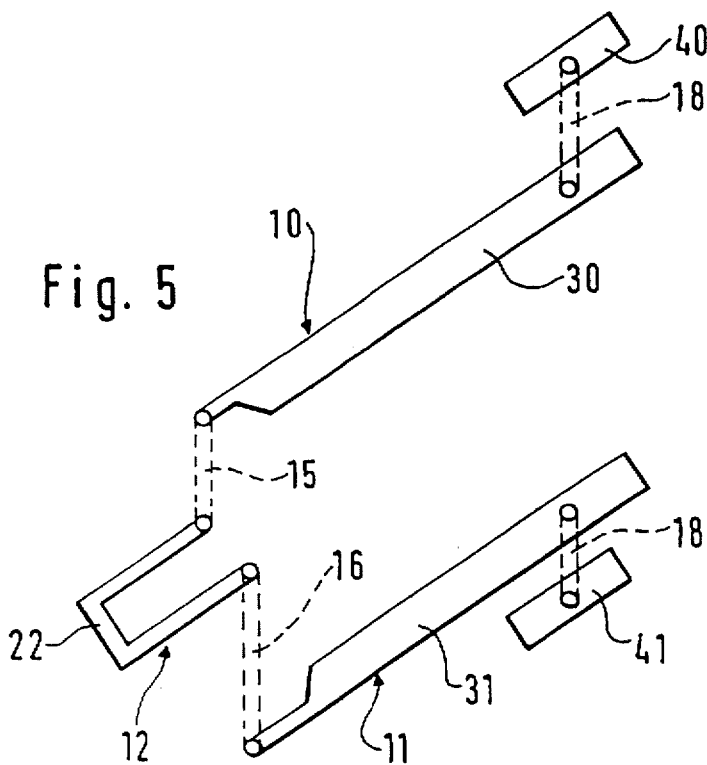
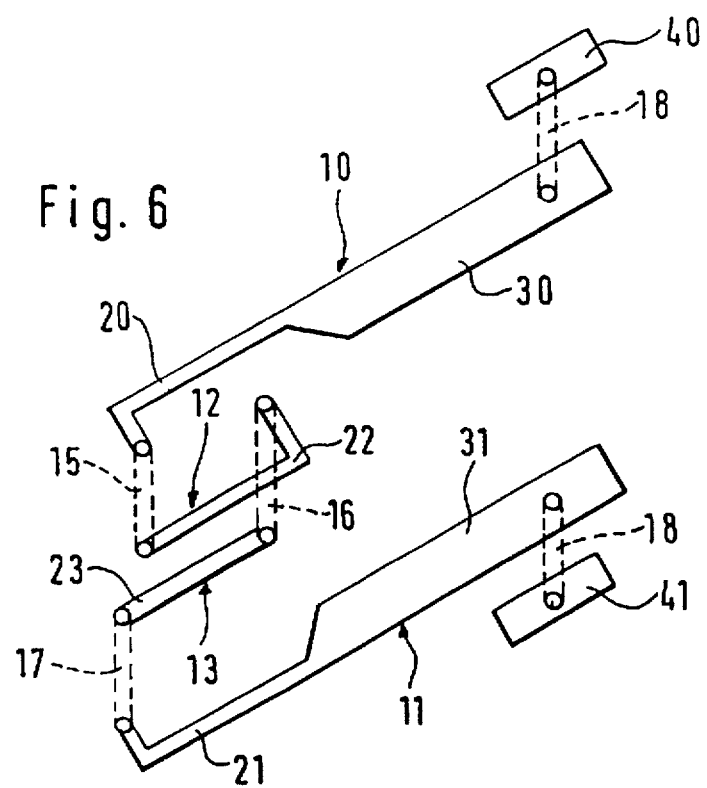

CERAMIC HEATER FOR A GAS MEASURING SENSOR

BACKGROUND OF THE INVENTION

1. Field of the Invention

The invention is based on a heater arrangement for a measuring sensor for determining components in gases, particularly in exhaust gases of internal combustion engines, according to the generic type of the main claim.

2. Description of the Related Art

From DE-OS 2,913,866 it is known, in a planar measuring sensor, to dispose two heating elements electrically insulated from the measuring element and among themselves by an insulating layer in two planes, one above the other. Each of the two heating elements uses a heat-conducting track and two heater connection tracks, which are positioned with respect to the side of the measuring sensor facing away from the measured gas such that they can respectively be connected to a current source there.

SUMMARY OF THE INVENTION

In contrast, the heater arrangement having the characterizing features of the main claim has the advantage that the heating capacity is increased, so that the measuring sensor possesses a shorter readying time for regulation. Particularly when used as rod heaters in lambda sensors, an improvement in the sensitivity with respect to impurities is additionally achieved.

Advantageous modifications and improvements of the heater arrangement disclosed in the main claim are possible with the measures outlined in the dependent claims. A particularly high heating capacity can be attained when the heat-conductor tracks of the individual heating elements are configured to have at least partially a meandering shape. A particularly homogenous temperature distribution is achieved when, with a heat-conducting track segment guided inside and one guided outside, the inside heat-conducting track segment is configured to be wider than the outside heat-conducting track. To avoid thermal overload, it is advisable to make the spacings of two adjacent heat-conducting tracks in one plane as large as possible, and the heat-conducting tracks have a minimum spacing from the edge of the ceramic substrate.

BRIEF DESCRIPTION OF THE DRAWING

A plurality of embodiments of the invention are represented in the drawing and described in detail in the following description.

FIG. 5 shows an exploded representation of a heating element disposed between two heater connection tracks, and FIG. 6 shows an exploded representation of four heating elements.

DESCRIPTION OF THE PREFERRED EMBODIMENTS

Figure 1:
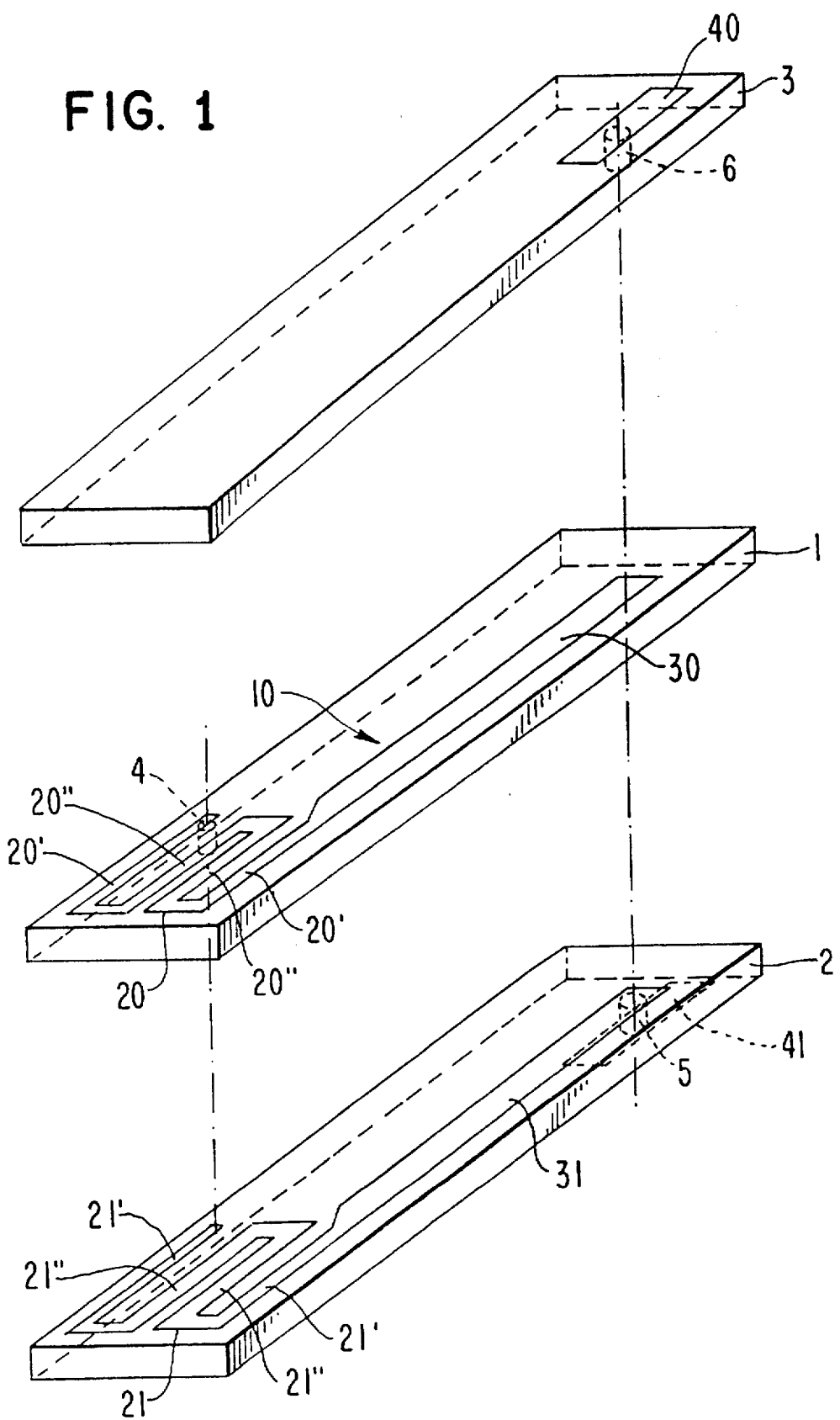
FIG. 1 shows an exploded representation of two heating elements, each having a heat-conducting track that has an inside and an outside segment.

The embodiments represented in the drawing each show heating elements having the course of a heat-conducting track, heater connection tracks and heater terminals; but not the ceramic insulating layers disposed between the heating elements. In conjunction with the exploded representations, however, it is easily conceivable that a ceramic insulating layer be disposed, on the one hand, between the heating elements and, on the other hand, the heating elements and heater terminals.

The embodiment according to FIG. 1 shows a first heating element 10 and a second heating element 11. An insulating layer 1 is disposed between the two heating elements 10 and 11. The insulating layer 1 is composed of, for example, one or a plurality of ceramic wafers of $Al_2O_3$, onto whose two large surfaces the heating elements 10 and 11 are printed, for example by means of a tungsten printing paste.

The two heating elements 10 and 11 each have a heat-conducting track 20, 21 and a heater connection track 30, 31. The heat-conducting track 20, 21 extends on the two large surfaces of respective ceramic substrates 1, 2 in such a manner that respectively two parallel-extending heat-conducting track segments are at the edge of the ceramic wafers 1, 2, between which an inwardly-guided, heat-conducting track segment having a meandering shape lies.

Figure 2:
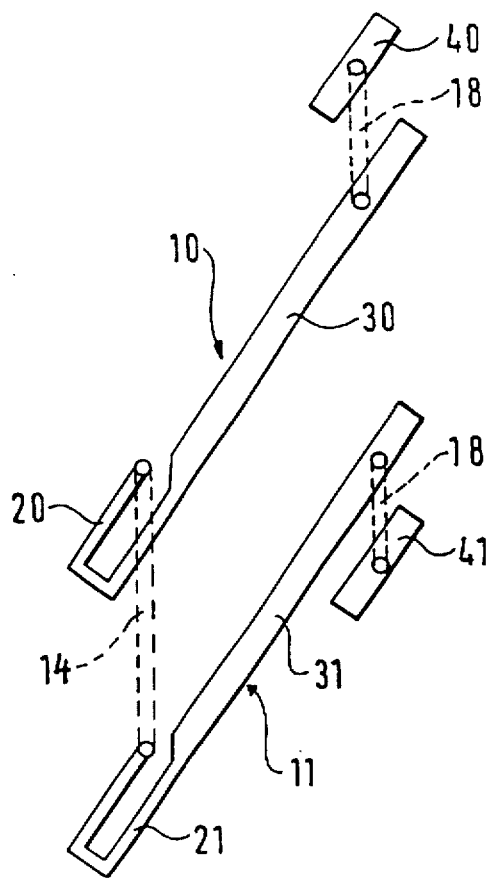
FIG. 2 shows an exploded representation of two heating elements, each having a heat-conducting track extending at the edge of a ceramic substrate.

The two heating elements 10 and 11 are preferably aligned with one another, so that the end of the heat-conducting track 20 of the first heating element 10 comes to rest above the end of the heat-conducting track 21 of the second heating element 11. At this location a hole 4 is provided in the insulating layer, through which one contacting member 14, a so-called via, is laid (as shown in FIG. 2). An electrical connection between the first heating element 10 and the second heating element 11 is thus produced. The contacting member 14 can be produced by, for example, dripping a tungsten paste into the hole provided in the insulating layer. Heat-conducting tracks 20, 21 may have segments having different widths. The width of interior track segments 20", 21" is preferably greater than that of exterior track segments 20', 21'.

In the present embodiment, a further ceramic insulating layer 3 for example of $Al_2O_3$, is respectively disposed on the first heating element 10 and the second heating element 11. Located on the insulating layer 3 covering the first heating element 10 is a first heater terminal 40, and on the insulating layer 2 covering the second heating element 11 is a second heater terminal 41. A further hole, in which respectively a further contacting member 18 for electrically connecting the heating arrangement 40, 41 to the heater connection tracks 30, 31 is disposed (see FIG. 2), is provided in each of the two insulating layers 3, 2. The two heater terminals 40, 41 are likewise printed onto the two insulating layers 3, 2 by means of a tungsten paste. The two heater terminals 40, 41 are thus bare and can be used for contact with electrical connections.

The embodiment according to FIG. 2 has essentially the same design as the embodiment in FIG. 1, but the heat-conducting tracks 20 and 21 of the two heating elements 10 and 11 are guided differently. In this embodiment the heat-conducting tracks 20 and 21 respectively have larger spacing than in the embodiment in FIG. 1. The heat-conducting tracks 20 and 21 are respectively guided along the edge of the insulating layers 1, 2 (not shown).

Figure 3:
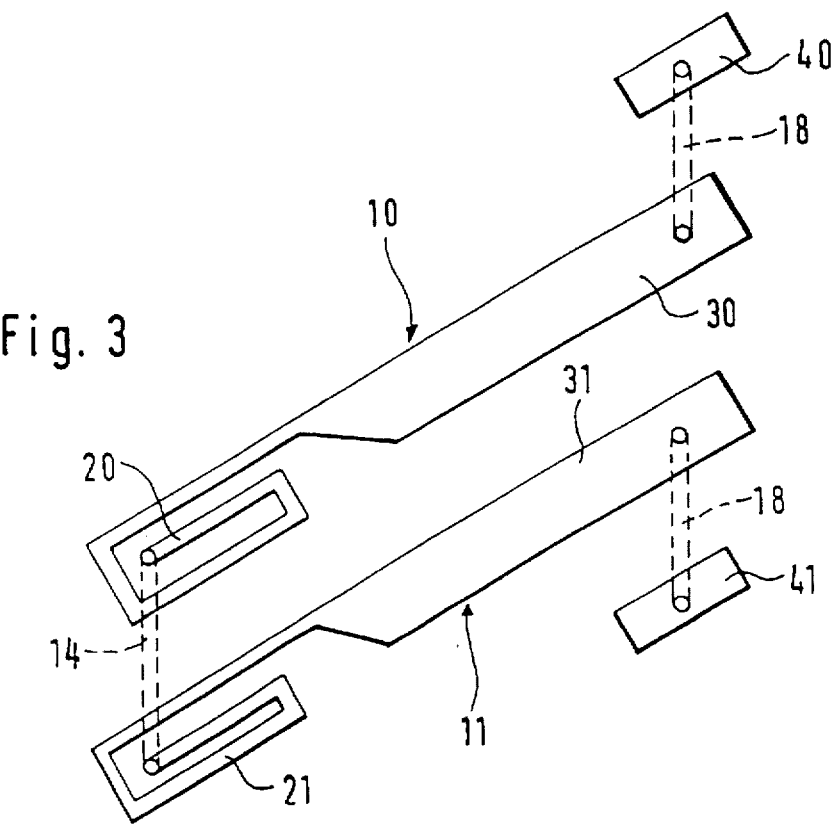
FIG. 3 shows an exploded representation of two heater elements, each having a heat-conducting track extending to the inside from the outside.

FIG. 3 shows a further embodiment of the heat-conducting tracks, in which the first and the second heat-conducting track 20, 21 are both guided along the edge of the insulating layer, and respectively back in the direction of the front edge of the insulating layer with a heat-conducting track segment, so that the two ends of the heat-conducting tracks 20 and 21 come to lie one above the other in the center of the front region of the insulating layer. In this embodiment the spacing of the heat-conducting track 20, 21 is respectively between that of the embodiments in FIGS. 1 and 2.

Figure 4:
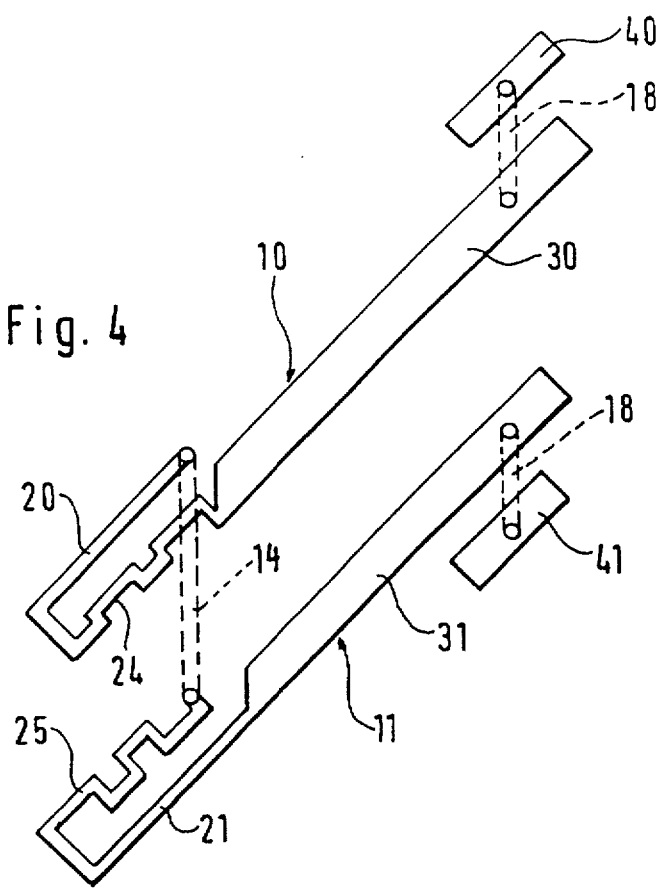
FIG. 4 shows a special embodiment of the heater arrangement according to FIG. 2, in which respectively an outside heat-conducting track has a meandering-shaped course.

A further embodiment of the heat-conducting tracks according to the embodiment shown in FIG. 2 is based on FIG. 4. In this instance the heat-conducting tracks 20 and 21 likewise extend at the edge of the insulating layer, and respectively one of the longitudinal segments of the heat-conducting track has a meandering course 24, 25. The longitudinal segment having the meandering course 24, 25 is configured such that the meandering course 24 of the first heating element 10 is located opposite the straight segment of the heat-conducting track 21 of the second heating element 11, and the meandering segment 25 of the second heating element 11 is located opposite the straight segment of the heat-conducting track 20 of the first heating element 10. Because of this embodiment, a more intense temperature field is created toward the narrow sides of the heater arrangement than in the previously-described embodiments. In the embodiments shown in FIGS. 1 through 4, the ends of the first heat-conducting track 20 and the second heat-conducting track 21 are located respectively aligned one above the other, so that the contacting member 14 is effected as already described in the first embodiment according to FIG. 1.

A further embodiment is shown in FIG. 5. In this instance the first heating element 10 and the second heating element 11 have only one heater connection track 30, 31. The first heater connection track 30 is disposed on a first insulating layer, not shown. The second heater connection track 31 is located on a second insulating layer, likewise not shown. A third heating element 12 is located between the two insulating layers. The third heating element 12 is formed from only one heat-conducting track 22 that extends at the edge of the two insulating layers, so that the heat-conducting track 22 ends above the end of the first heater connection track 30 and above the end of the second heater connection track 31. The ends of heat-conducting track 22 and heater connection tracks 30, 31, which are disposed one above the other, are respectively connected to one another by means of a first and a second contacting member 15, 16. The contacting members 15, 16 are effected in the same way as described in the embodiment according to FIG. 1. The same applies for the arrangement and production of the heater terminals 40, 41 and the terminal contacting members 18.

Finally, an embodiment follows from FIG. 6 in which four heating elements 10, 11, 12 and 13 are provided. Each of the heating elements 10, 11, 12 and 13 lies in respectively one plane and is separated from the adjacent heating element by means of an insulating layer, not shown. The first and second heating elements 10, 11 respectively have, as already described in the previous embodiments, one heat-conducting track 20, 21 and one heater connection track 30, 31. The heat-conducting tracks 20, 21 extend symmetrically with respect to a plane of symmetry perpendicular to the plane of the layer. The heat-conducting tracks 20, 21 each have a segment that extends along the longitudinal side of the insulating layer and a segment that extends at a right angle thereto along the narrow side of the insulating layer. The third heating element 12 disposed beneath the first heating element 10 extends from the projection of the end of the first heat-conducting track 20 along the longitudinal side of the insulating layer, and bends at a right angle, in the direction of the longitudinal side located opposite, to beneath the first heat-conducting track 20. The fourth heat-conducting track 23 extends along the longitudinal side of the insulating layer, and begins at the location of the projection of the second end of the third heat-conducting track 22, and ends at the location of the projection of the end of the second heat-conducting track 21. Hence, the ends of the heat-conducting tracks 20, 21, 22, 23 lie one above the other in such a way that an electrical connection is possible by means of the first, second and third contacting members 15, 16, 17 extending through the insulating layers. The embodiment of the contacting members 15, 16, 17, and the embodiment of the heater terminals 40, 41, as well as the associated terminal contacting members 18, are effected as already described in the first embodiment.

It is also conceivable, in addition to the insulating layers, to dispose the heater arrangement on further ceramic substrate layers. Likewise, the insulating layers disposed on the first and second heating elements 10, 11 can be replaced by thermally well-conductive ceramic layers. Furthermore, it is conceivable to lay the electrical terminals directly onto the heater connection tracks 30, 31.

The application of the invention is not limited to the described rod heaters for lambda finger sensors. It is also conceivable to configure the heater arrangement for planar sensors, in which case one of the outer-lying heating elements is connected to a measuring element in an electrically-insulated manner. Such measuring elements can be, for example, potentiometric or polarographic sensor elements or resistance measuring sensors.

What is claimed is:

1. A ceramic heater for a measuring sensor for determining components in gases including exhaust gases of internal combustion engines, comprising:

first and second ceramic substrates which are stacked with respect to one another, at least one additional ceramic substrate provided between the first and second ceramic substrates, and a third ceramic substrate which is positioned on top of the first ceramic substrate and functions as a cover layer, the first, the second, the third, and the at least one additional ceramic substrate having defined therein respective first, second, third, and at least one additional through-holes;

a first heater element consisting essentially of a heater connection track which is provided on a surface of the first ceramic substrate;

a second heater element consisting essentially of a heater connection track which is provided on a surface of the second ceramic substrate;

at least one additional heater element consisting of a heat-conducting track which is provided on a respective surface of one of the at least one additional ceramic substrate;

a first heater terminal provided on a surface of the third ceramic substrate which is oriented outwardly of the ceramic heater and a second heater terminal provided on a surface of the second ceramic substrate which is oriented outwardly of the ceramic heater;

a contacting member positioned within the first through-hole and in contact with the heater connection track of the first heater element and the heat-conducting track of the at least one additional heater element;

at least one additional contacting member each positioned within a respective at least one additional through-hole in the at least one additional ceramic substrate and in contact with the heat-conducting track of the at least one additional heater element and the heater connection track of the second heating element whereby the respective heater elements are electrically connected in series with one another; and further contacting members positioned respectively within the second and third through-holes and in contact with respective heater connection tracks of the first and second heater elements, whereby the first and second heater elements are electrically connected to respective heater terminals.

2. The ceramic heater according to claim 1, wherein a plurality of the at least one additional ceramic substrate is provided, each additional ceramic substrate having a heater element consisting essentially of a heat-conducting track provided on a surface thereof and having respective through-holes defined therein, and the heater elements being disposed at least partly one above the other with a respective ceramic substrate positioned therebetween to provide electrical insulation, and wherein further contacting members are positioned within respective ones of the respective through-holes and in contact with respective heat-conducting tracks whereby the heat-conducting tracks are electrically connected in series with one another.

3. The ceramic heater according to claim 2, wherein the respective heat-conducting tracks have a path having at least one shape selected from the group consisting of a meandering shape and a zig-zag shape.

4. The ceramic heater according to claim 1, wherein the respective heat-conducting tracks each have at least one interior and at least one exterior heat-conducting track segment provided respectively in interior and exterior regions of the surfaces of respective ceramic substrates and having respective widths, and wherein the width of respective at least one interior heat-conducting track segments is greater than the width of respective at least one exterior heat-conducting track segments.

5. The ceramic heater according to claim 1, wherein the first, second, and at least one additional heater elements are resistance heaters which have a layer form.

6. A ceramic heater for a measuring sensor for determining components in gases including exhaust gases of internal combustion engines, comprising:

first and second ceramic substrates which are stacked with respect to one another, at least one additional ceramic substrate provided between the first and second ceramic substrates, and a third ceramic substrate which is positioned on top of the first ceramic substrate and functions as a cover layer, the first, the second, the third, and the at least one additional ceramic substrate having defined therein respective first, second, third, and additional through-holes;

a first heater element which is provided on a surface of the first ceramic substrate and which has a heat-conducting track and a heater connection track in contact with one another;

a second heater element which is provided on a surface of the second ceramic substrate and which has a heat-conducting track and a heater connection track in contact with one another;

at least one additional heater element consisting of a heat-conducting track provided on a respective surface of one of the at least one additional ceramic substrate;

a first heater terminal provided on a surface of the third ceramic substrate which is oriented outwardly of the ceramic heater and a second heater terminal provided on a surface of the second ceramic substrate which is oriented outwardly of the ceramic heater;

a contacting member positioned within the first through-hole and in contact with the heat-conducting track of the first heater element and the heat-conducting track of the at least one additional heater element;

at least one additional contacting member positioned within a respective at least one additional through-hole in the at least one additional ceramic substrate and in contact with the conducting tracks of adjacent heater elements; and further contacting members positioned respectively within the second and third through-holes and in contact with respective heater connection tracks of the first and second heater elements whereby the first and second heater-elements are electrically connected to respective heater terminals.

7. The ceramic heater according to claim 6, where in two additional heater element, are provided, wherein the respective heat-conducting tracks of the first, the second and the two additional heater elements have respective ends, and wherein two additional contacting members are provided, each of the two additional contacting members connecting the end of one heat-conducting track of one heating element to the end of another heat-conducting track of another heating element.

8. The ceramic heater according to claim 6, wherein the respective heat-conducting tracks have a path having at least one shape selected from the group consisting of a meandering shape and a zig-zag shape.

9. The ceramic heater according to claim 6, wherein the respective heat-conducting tracks each have at least one interior and at least one exterior heat-conducting track segment provided respectively in interior and exterior regions of the surfaces of the respective ceramic substrates and having respective widths, and wherein the width of respective at least one interior heat-conducting track segments is greater than the width of respective at least one exterior heat-conducting track segments.

10. The ceramic heater according to claim 6, wherein the first, the second, and the at least one additional c heating elements are resistance heaters which have a layer form.

* * * * *